United States Patent [19]

Brewer

[11] Patent Number: 5,792,200
[45] Date of Patent: Aug. 11, 1998

[54] ADAPTIVE MODE SWITCHING IN A RATE-ADAPTIVE PACEMAKER AND HYSTERESIS FOR MODE SWITCHING

[75] Inventor: Maurice A. Brewer, Houston, Tex.

[73] Assignee: Sulzer Intermedics Inc., Angleton, Tex.

[21] Appl. No.: 847,913

[22] Filed: Apr. 28, 1997

[51] Int. Cl.$^6$ .................................. A61N 1/365
[52] U.S. Cl. ........................... 607/20; 607/18; 607/17; 607/19
[58] Field of Search .................. 607/17, 14, 18, 607/19, 20, 21-24

[56] References Cited

U.S. PATENT DOCUMENTS

| | | | |
|---|---|---|---|
| 4,527,568 | 7/1985 | Rickards | 128/419 |
| 4,846,195 | 7/1989 | Alt | 128/782 |
| 4,856,523 | 8/1989 | Sholder et al. | 128/419 |
| 4,926,863 | 5/1990 | Alt | 128/419 |
| 5,052,388 | 10/1991 | Sivula et al. | 128/419 |
| 5,144,949 | 9/1992 | Olson | 607/17 |
| 5,350,409 | 9/1994 | Stoop et al. | 607/17 |
| 5,391,189 | 2/1995 | van Krieken et al. | 607/17 |

OTHER PUBLICATIONS

Intermedics; A Company of Sulzermedica; Marathon™ Dual-Chamber Rate-Adaptive Pulse Generators;; (8p.); Jan. 1996.

Intermedics; A Company of Sulzermedica; Marathon™ The New Gold Standard in Pacing; Brochure with insert pages; Jan. 1996.

Primary Examiner—William E. Kamm
Assistant Examiner—Kennedy J. Schaetzle
Attorney, Agent, or Firm—John R. Merkling; Conley, Rose & Tayon

[57] ABSTRACT

A programmable pacemaker and program therefor are disclosed, wherein the pacer is programmed to operate in a first pacing mode whenever the measured atrial rate is less than a certain threshold switching rate $R_T$, and to operate in a second pacing mode whenever the measured atrial rate is greater than the threshold switching rate $R_T$. The threshold switching rate $R_T$ is varied based on either a programmed algorithm or the measured value of one or more sensed parameters. In another embodiment, a hysteresis is introduced, so that the rate at which the pacer switches back to its low-activity mode is lower than the rate that triggers a switch to the high-activity mode.

25 Claims, 6 Drawing Sheets

ADAPTIVE MODE SWITCHING IN A RATE-ADAPTIVE PACEMAKER AND HYSTERESIS FOR MODE SWITCHING

BACKGROUND OF THE INVENTION

1. Field of the Invention

The present invention relates generally to cardiac stimulating devices, such as pacemakers and defibrillators. More particularly, the present invention relates to a cardiac stimulating device that is capable of operating in more than one mode and is capable of switching between modes. Still more particularly, the present invention relates to a cardiac stimulating system that adapts the criteria that drive the automatic mode switch in response to changes in activity level.

2. Description of the Related Art

Figure 1:
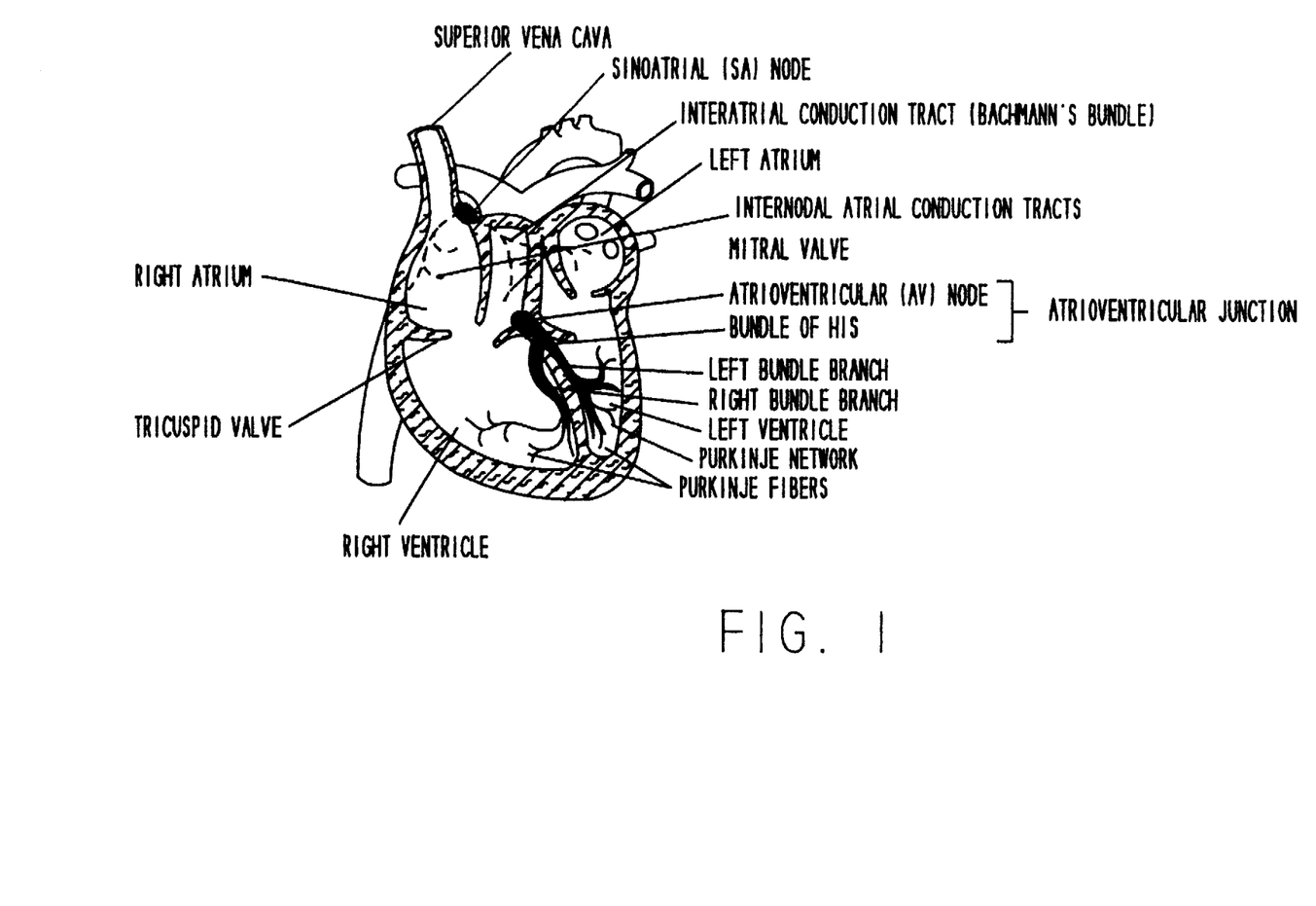
FIG. 1 is a schematic cut-away view of a human heart, in which the various relevant parts are labeled.

In the normal human heart, illustrated in FIG. 1, the sinus (or sinoatrial (SA)) node generally located near the junction of the superior vena cava and the right atrium constitutes the primary natural pacemaker by which rhythmic electrical excitation is developed. The cardiac impulse arising from the sinus node is transmitted to the two atrial chambers (or atria) at the right and left sides of the heart. In response to this excitation, the atria contract, pumping blood from those chambers into the respective ventricular chambers (or ventricles). The impulse is transmitted to the ventricles through the atrioventricular (AV) node, and via a conduction system comprising the bundle of His, or common bundle, the right and left bundle branches, and the Purkinje fibers. The transmitted impulse causes the ventricles to contract, the right ventricle pumping unoxygenated blood through the pulmonary artery to the lungs, and the left ventricle pumping oxygenated (arterial) blood through the aorta and the lesser arteries to the body. The right atrium receives the unoxygenated (venous) blood. The blood oxygenated by the lungs is carried via the pulmonary veins to the left atrium.

This action is repeated in a rhythmic cardiac cycle in which the atrial and ventricular chambers alternately contract and pump, then relax and fill. Four one-way valves, between the atrial and ventricular chambers in the right and left sides of the heart (the tricuspid valve and the mitral valve, respectively), and at the exits of the right and left ventricles (the pulmonic and aortic valves, respectively, not shown) prevent backflow of the blood as it moves through the heart and the circulatory system.

The sinus node is spontaneously rhythmic, and the cardiac rhythm originating from the primary natural pacemaker is termed sinus rhythm. This capacity to produce spontaneous cardiac impulses is called rhythmicity, or automaticity. Some other cardiac tissues possess this electrophysiologic property and hence constitute secondary natural pacemakers, but the sinus node is the primary pacemaker because it has the fastest spontaneous rate. The secondary natural pacemakers tend to be inhibited by the more rapid rate at which impulses are generated by the sinus node.

The resting rates at which sinus rhythm occurs in normal persons differ between age groups, generally ranging between 110 and 150 beats per minute ("bpm") at birth, and gradually slowing to the range between 65 and 85 bpm usually found in adults. The resting sinus rate (hereinafter termed simply the "sinus rate") varies from one person to another, and despite the aforementioned usual adult range, is generally considered to lie anywhere between 60 and 100 bpm (the "sinus rate range") for the adult population.

A number of factors may affect the rate of sinus rhythm within the sinus rate range, and some of those factors may slow or accelerate the rate sufficiently to take it outside the sinus rate range. The slower rates (below 60 bpm) are called sinus bradycardia, and the higher rates (above 100 bpm) are termed sinus tachycardia. In particular, sinus tachycardia observed in healthy persons arises from various factors which may include physical or emotional stress (exercise or excitement), consumption of beverages containing alcohol or caffeine, cigarette smoking, and ingestion of certain drugs. The sinus tachycardia rate usually ranges from 101 to 160 bpm in adults, but has been observed at rates up to (and in infrequent instances, exceeding) 200 bpm in younger persons during strenuous exercise.

Sinus tachycardia is sometimes categorized as a cardiac arrhythmia, since it is a variation from normal sinus rate range. Arrhythmia rates which exceed the upper end of the sinus rate range are termed tachyarrhythmias. Healthy persons usually experience a gradual return to the sinus rate after removal of the factor(s) giving rise to sinus tachycardia. Hence, treatment of the arrhythmia is not necessary unless it is found to be attributable to disease. Abnormal arrhythmias (which are hereinafter simply termed "arrhythmias", and in the case of abnormal tachyarrhythmias, simply termed "tachyarrhythmias", to mean arrhythmias associated with cardiac or other disease), however, may require special treatment, and in some instances require immediate emergency treatment toward preventing sudden death of the afflicted individual.

Disruption of the natural pacemaking and propagation system as a result of aging or disease is commonly treated by artificial cardiac pacing, by which rhythmic electrical discharges are applied to the heart at a desired rate from an implanted artificial pacemaker. An artificial pacemaker (or "pacer" as it is commonly labeled) is an implantable medical device which delivers electrical pulses to an electrode that is implanted adjacent or into the patient's heart in order to stimulate the heart so that it will beat at a desired rate. If the body's natural pacemaker performs correctly, blood is oxygenated in the lungs and efficiently pumped by the heart to the body's oxygen-demanding tissues. However, when the body's natural pacemaker malfunctions, an implantable pacemaker often is required to properly stimulate the heart. An in-depth explanation of certain cardiac physiology and pacemaker theory of operation is provided in U.S. Pat. No. 4,830,006.

Figure 2:
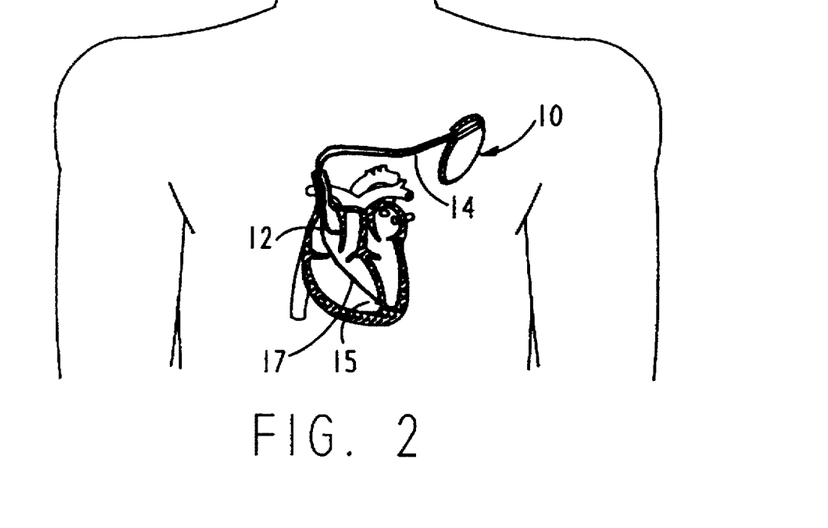
FIG. 2 is a schematic diagram of a dual-chamber pacer implanted in a human body.
Figure 3:
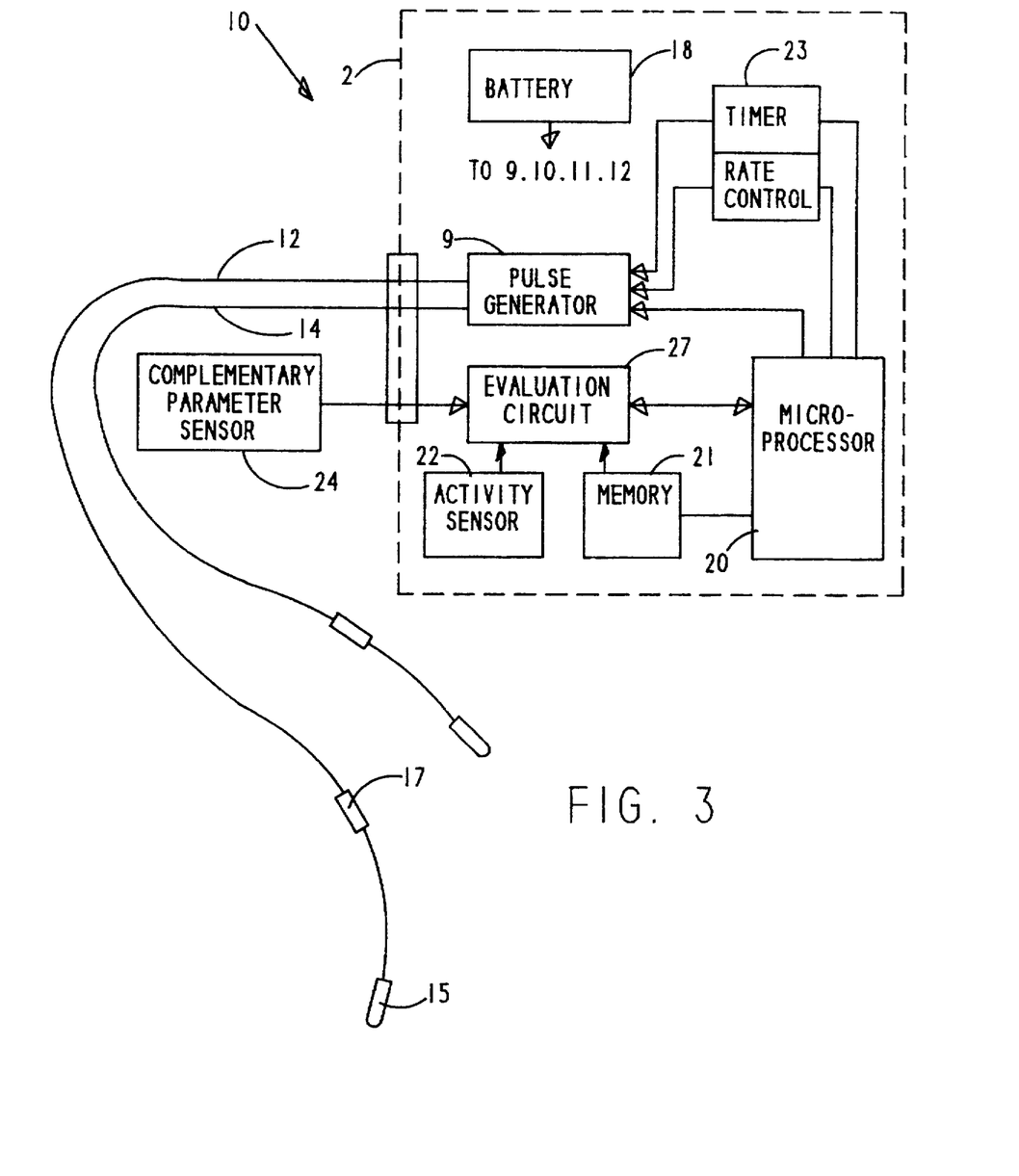
FIG. 3 is a block diagram of the pacer of FIG. 2.

Referring now to FIGS. 2 and 3, a typical pacemaker 10 comprises a battery 18 coupled electrically to the heart via one or more pacing leads 12, 14. Transmission of electrical signals through the leads is controlled by a microprocessor 20. In addition to the microprocessor 20, the pacer may also include a memory device 21, such as random access memory (RAM) chips or 30 the like, and an evaluation circuit 27. Pacemaker 10 may have the capability of monitoring physiological parameters of the patient via a conventional activity sensor 22 and/or a complementary parameter sensor 24, and may store digital signals representative of these parameters in the memory device 21. When prompted by an external programmer/reader (not shown), the processing circuitry can transmit the contents of the memory device to the external programmer/reader for analysis by the physician. According to conventional digital processing techniques, a clock signal is provided by an internal timer 23 that synchronizes the activities of the processing circuitry and memory.

By way of example only, in FIGS. 2 and 3, two leads 12, 14 are shown connecting a conventional pacemaker 10 to the heart. In a conventional dual chamber arrangement, leads 12, 14 are inserted in the right atrium and right ventricle, respectively. Each lead 12, 14 includes at least one stimulating electrode(s) for delivery of electrical impulses to excitable myocardial tissue in the appropriate chamber(s) inside the right side of the patient's heart. As shown in FIGS. 2 and 3, each lead 12, 14 includes two electrodes, for example tip electrode 15 and ring electrode 17 on lead 12, to provide a total of four electrodes in the heart. Two-, three-, and four-terminal devices all have been used or suggested as possible electrode schemes. Those skilled in the art will recognize that the pacing apparatus described herein is representative of a variety of devices. The present disclosure is provided merely to establish a context for the description of the invention below and is not intended to limit the scope of the invention in any way.

Pacers today are typically designed to use one of three different response types, namely, asynchronous (fixed rate), inhibited (stimulus generated in absence of specified cardiac activity), or triggered (stimulus delivered in response to specified cardiac activity). Broadly speaking, the inhibit and triggered pacemakers may be grouped as "demand" type pacemakers, in which a pacing pulse is only generated when demanded by the heart. Typically, demand pacemakers sense the patient's natural atrial rate and apply stimuli only during periods when the atrial rate falls below the desired pacing rate. In a demand pacer electrodes in the leads 12, 14 sense the occurrence of a natural pacing event and transmit this to the microprocessor 20. Pacemakers range from the simple fixed rate, single chamber device that provides pacing with no sensing function, to highly complex models that provide fully automatic dual chamber pacing and sensing functions. The latter type of pacemaker is the latest in a progression toward physiologic pacing, that is, the mode of artificial pacing that most closely simulates natural pacing.

The data provided by sensors 22, 24 allows the pacer to adapt to the changing demands of the body through modulation of the pacing rate. Rate modulation is designed to help the patient adapt to physiologic stress, such as exertion, with an increase in heart rate, even if the patient's intrinsic sinus mode would not otherwise allow this to occur. Rate modulation depends on the sensing of a physiologic indicator by an appropriate sensor (such as sensors 22, 24) and use of the sensed value in a rate-controlling algorithm in the software of the pacer. Examples of possible physiologic indicators include motion of the body, body temperature, blood oxygen and respiratory rate. Rate modulation is a common feature in pacers today.

Because of the number of options available in pacer design, a convention has been established whereby specific pacer configurations are identified according to a code comprising three, four or five letters. The fifth code position describes the antitachycardia functions, if any. Because this position is not applicable to most commonly used pacemaker types, most common codes comprise either three or four letters. For this reason and for simplicity's sake, the fifth code position is omitted from the following table. Each code can be interpreted as follows:

| Code position | 1 | 2 | 3 | 4 |
|---|---|---|---|---|
| Function identified | chamber paced | chamber sensed | response to sensing | programmability, rate modulation |
| Options available | O - none<br>A - atrium<br>V - ventricle<br>D - dual | O - none<br>A - atrium<br>V - ventricle<br>D - dual | O - none<br>T - triggered<br>I - inhibited | O - none<br>P - programmable<br>M - multi- |

| Code position | 1 | 2 | 3 | 4 |
|---|---|---|---|---|
| | (A + V) | (A + V) | D - dual<br>(T + I) | programmable<br>C - communicating<br>R - rate modulating |

For example, a VVI pacer paces and senses in the ventricle and uses an inhibited type response, i.e. pacing is inhibited by sensed spontaneous electrical activation of the ventricle. Similarly, a VVIR pacer paces and senses in the ventricle and uses an inhibited type response, but is also capable of modulating its rate activity in response to metabolic demand. Of the many possible pacer configurations, four or five are most commonly used. These are VVI, VVIR, DVI, DDD and DDDR. In general, it is desirable to provide pacing only when needed and to avoid unnecessary stimulation of the heart, both to avoid causing arrhythmia and to avoid unnecessary drains on the pacer's power supply.

Despite the adaptability provided by a rate modulation algorithm, it has been found that an optimal pacing function sometimes also requires switching between modes. For example, patients with AV block may have a normal sinus rhythm at lower atrial rates but experience exercise-induced, pathological atrial tachycardias at higher atrial rates. Thus, dual-chamber pacing may be indicated at the lower rates, while single-chamber pacing is indicated and appropriate at the higher rates. It is known that at even higher atrial rates, tracking of the atrial contractions with one-to-one ventricular contractions results in inefficient emptying of the ventricles. Thus, at these rates, it may be desirable to avoid ventricular tracking of the atria and instead pace the ventricles independently at a steady, lower rate. Also, in order to conserve energy (prolong battery life) and avoid unnecessarily stimulating the heart, it is desirable to operate in a mode that provides a minimum acceptable level of pacing. Thus, in this instance, it would be desirable to switch modes from DDD or DDDR to VVI or VVIR at some threshold rate.

For these reasons, it is sometimes desired to provide a pacer that is capable of switching modes spontaneously. To this end, pacers have been developed that can be programmed to switch modes (from DDD to VVIR, as one example) at a certain, preset atrial rate. U.S. Pat. No. 4,856,523, for example, discloses a pacemaker in which mode switching occurs automatically and is based on a comparison of the average atrial rate over n beats to a predetermined, threshold value. (See FIG. 1C and column 8, line 42 to column 9, line 32). The threshold rate at which switching occurs is entered during programming of the pacer upon installation and remains fixed thereafter. It has been found however, that the optimal use of mode switching is enhanced by allowing some variability in the threshold rate at which switching occurs. Specifically, it is sometimes desirable to vary the threshold mode switching rate on the basis of either a programmed algorithm or the measured value of one or more sensed parameters.

SUMMARY OF THE INVENTION

A method is disclosed whereby a pacemaker switches modes automatically in response to the detection of one or more indicators, which indicators can include atrial rate, ventricular rate, and or various physiologic indicators or combinations thereof. The present method reduces the incidence of undesirable mode switches by basing the switching criteria on preselected, customized variables, the values of which are themselves dependent on one or more physiologic factors.

According to a preferred embodiment, a threshold switching rate is calculated as a function of the programmed base pacing rate. Because the base pacing rate is typically a non-linear function of activity level, the threshold switching rate is also nonlinear and dependent on activity level. The threshold switching rate can be equal to the base pacing rate plus a constant, or can be some other, more complex function of the base pacing rate and/or activity level. In addition, hysteresis may be used in conjunction with the varying threshold switching rate, so as to prevent undesired toggling between pacing modes.

A pacer programmed in accordance with one preferred embodiment switches from DDD to VVIR mode whenever the measured atrial rate is above the calculated threshold switching rate, and operates in DDD mode whenever the measured atrial rate is below the calculated threshold switching rate.

The present invention comprises a combination of features and advantages which enable it to overcome various problems of prior devices and to advance the pacer art in substantial measure. The various characteristics described above, as sell as other features, will be readily apparent to those skilled in the art upon reading the following detailed description of the preferred embodiments of the invention, and by referring to the accompanying drawings.

BRIEF DESCRIPTION OF THE DRAWINGS

Other objects and advantages of the invention will become apparent upon reading the following detailed description and upon reference to the accompanying drawings, wherein.

DETAILED DESCRIPTION OF THE PREFERRED EMBODIMENT

Figure 4A:
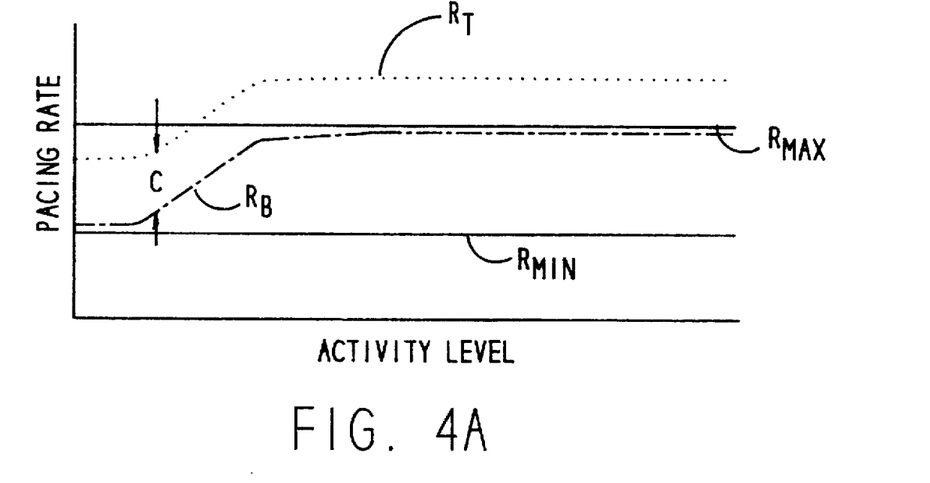
FIG. 4A is a plot showing the relationship between the mode switching rate and the base pacing rate according to the present invention.

Referring now to FIGS. 3 and 4A, the plot shows typical limiting values and a rate-response pacing function. The horizontal axis indicates the activity rate A. The activity rate A is calculated by microprocessor 20 in response to input from sensor 22 and/or sensor 24, which measure various physiologic indicators as discussed above. The vertical axis in FIG. 4A indicates the paced rate, i.e. the rate at which the pacemaker would pace in the absence of spontaneous pacing by the heart itself. FIG. 4A shows a base programmed rate $R_{min}$ and a maximum pacing rate $R_{max}$, both of which have preprogrammed, constant values that are stored in memory device 21. Base programmed rate $R_{min}$ is the minimum pacing rate, which will be provided in the absence of physical activity. Maximum rate $R_{max}$ is a preset upper limit.

Varying between base programmed rate $R_{min}$ and maximum pacing rate $R_{max}$ is the rate-responsive base pacing rate $R_B$, which is a function of activity, as determined by one or more sensor outputs. $R_B$ is defined as $R_{min}$ plus a increment that can be based on any of a variety or combination of sensed parameters according to equation (1).

$$R_B = R_{min} + f(A) \tag{1}$$

Alternatively, $R_B$ can be defined as $R_{max}$ minus a function of activity f'(A). Several rate response algorithms for calculating $R_B$ are well known in the art. In the embodiment shown, the base pacing rate $R_B$ increases as the activity level A (as measured by sensor output) increases, from a minimum equal to the base programmed rate $R_{min}$ to a maximum less than or equal to the maximum pacing rate $R_{max}$. $R_B$ is calculated by microprocessor 20.

Still referring to FIG. 4A, the pacemaker is programmed to switch modes when the measured atrial rate $R_M$ (not shown) exceeds a threshold rate $R_T$. $R_M$ is determined in a conventional manner such as measurement of the time required to complete each beat cycle. According to the present invention, $R_T$ is programmed to be a function of the base pacing rate $R_B$ and thus is equal to the minimum pacing rate plus some function of the activity level. A pacemaker programmed according to the invention would automatically switch modes whenever the measured atrial rate $R_M$ exceeded $R_T$ for some predetermined number of consecutive beats n, and would maintain the second mode as long as the measured atrial rate did not drop below $R_T$ for more than n consecutive beats. By varying the mode-switch threshold rate $R_T$, as opposed to always switching at the same fixed rate, it is believed that a more efficient and effective physiologic pacing can be maintained without sacrificing battery life or unnecessarily stimulating the heart.

The function that defines the relationship between the base pacing rate $R_B$ and the variable mode-switch threshold rate can comprise the addition of a predetermined number to the base pacing rate. In this way, the same function that determines pacing rate $R_B$ determines the shape of the mode-switch threshold rate $R_T$. According to this embodiment, $$R_T = R_B + c, \tag{2}$$

where c is a constant. Alternatively, the value of c in Equation (1) can be a second function of activity level A. In such a case, c is preferably a nonlinear function of A. Because $R_B$ is a function of activity, $R_T$ is indirectly also a function of activity.

Figure 4B:
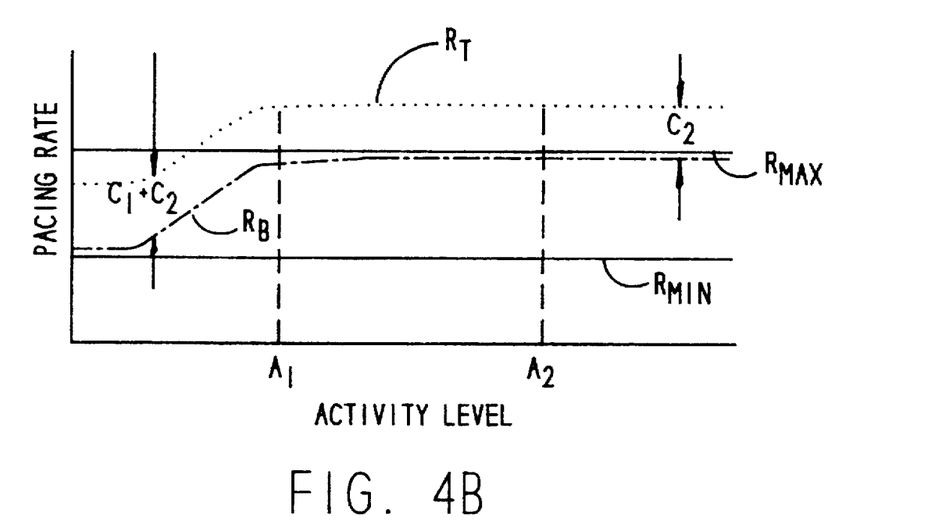
FIG. 4B is a plot showing an alternative embodiment of the relationship between the mode switching rate and the base pacing rate shown in FIG. 4A.

Alternatively, as shown in FIG. 4B, the function that defines the relationship between the base pacing rate $R_B$ and the variable mode-switch threshold rate can be defined as follows:

$$R_T = R_B + c_1(A_2 - A) + c_2 \text{ for } A_1 < A < A_2 \tag{3a}$$

$$R_T = R_B + (c_1 + C_2) \text{ for } A < A_1 \text{ and} \tag{3b}$$

$$R_T = R_B + c_2 \text{ for } A > A_2 \tag{3c}$$

where $A_1$ and $A_2$ are preprogrammed activity level constants. Equations (2a–c) produces an $R_T$ that approaches $R_B$ as the activity level goes from $A_1$ to $A_2$. According to the embodiment described by equations (2a–c), the difference between $R_T$ and $R_B$ varies linearly over a portion of the range of A and is constant outside that range, however it is also contemplated that the relationship between $R_T$ and $R_B$ can be non-linear. In some cases, it may also be preferred to provide a maximum $R_{Tmax}$ in the upper end of the range, above which the switching threshold $R_T$ cannot go.

It is also contemplated that the difference between $R_T$ and $R_B$ could increase over all or a portion of the range of $R_B$, but this mode is not presently preferred, as it is presently believed that the mode switch rate should become more attainable at higher heart rates, rather than less attainable.

In the foregoing discussion $R_T$ has been described as a function of $R_B$. As $R_B$ is a function of the measured activity level A, it will be understood that the principles of the present invention can also used in calculating $R_T$ directly as a function of A.

Figure 5:
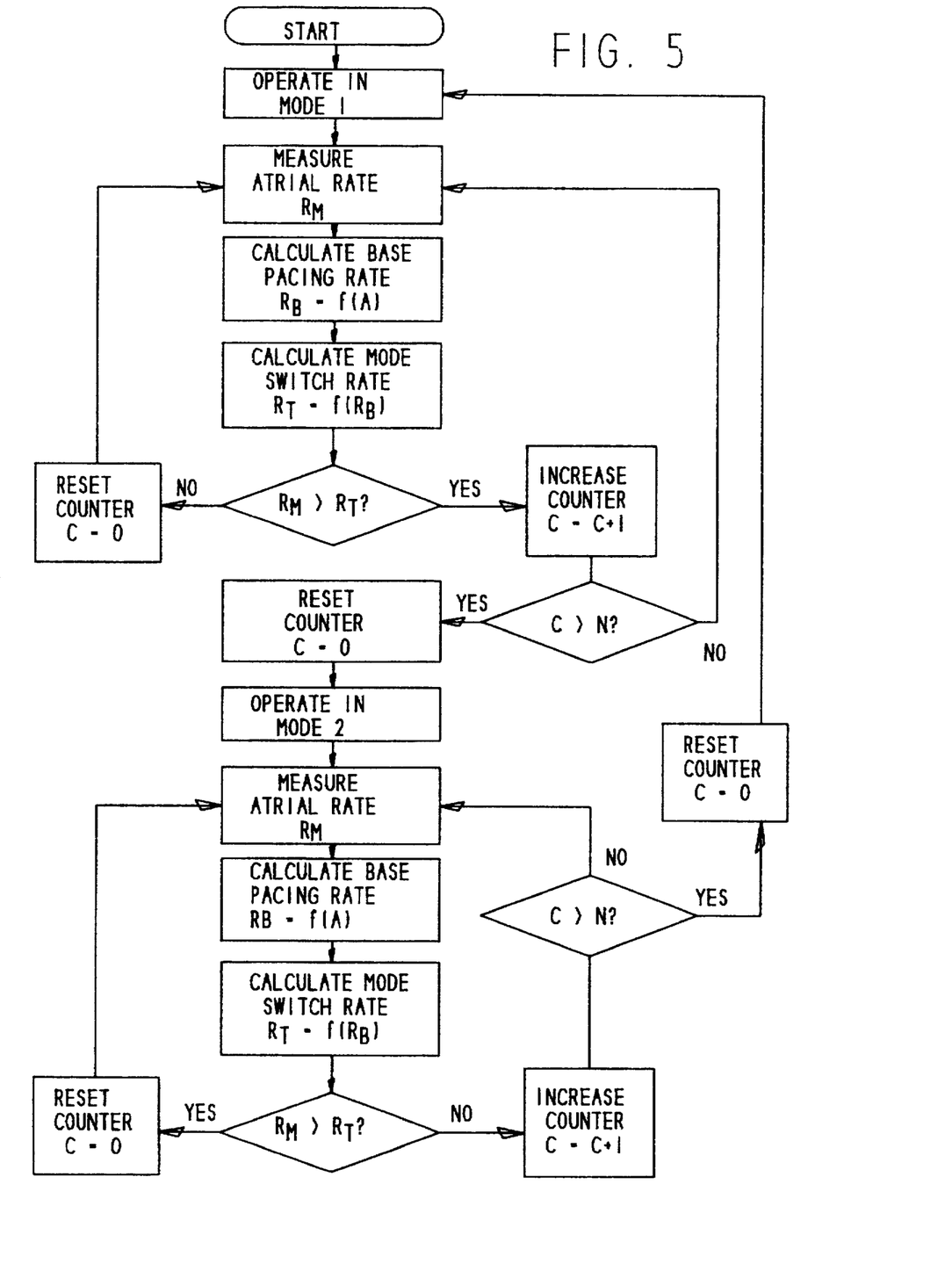
FIG. 5 is a flow chart representing the program steps associated with operating a pacer in accordance with the present invention.

As described above, pacemaker 10 includes a microprocessor 20 or equivalent circuitry that directs the carrying out of its desired functions. Thus, the implementation of the automatic mode switching feature of the present invention is readily carried out by incorporating a logic routine within the controlling programs of the pacemaker as summarized in the flow chart of FIG. 5. Specifically, in the embodiment illustrated in FIG. 5, pacemaker 10 initially paces in a first mode, Mode 1. The logic cycle for determining whether mode should occur begins with a measurement of the direct heat rate $R_M$ on the basis of sensed cardiac events that result in the transmission of signals from through leads 12, 14 to microprocessor 20. Next, the base pacing rate $R_B$ is calculated on the basis of outputs received from one or more activity sensors and the mode switching threshold rate $R_T$ is calculated on the basis of $R_B$. In the next step, $R_M$ is compared to $R_T$. If $R_M$ is less than $R_T$, the pacer continues to pace in Mode 1. If $R_M$ is greater, a counter value c is increased by one. If the counter value c is less than a predetermined integer n, the pacer continues to pace in Mode 1. If the counter value c is greater than n, the pacer commences operation in Mode 2. A corresponding series of steps is followed once the pacer is in Mode 2. During the course of operation, microprocessor 20 iterates continuously through this cycle, switching to Mode 2 whenever $R_M$ is greater than $R_T$ for more than n cycles and to Mode 1 whenever $R_M$ is less than $R_T$ for more than n cycles. The modes between which a pacer might switch according to this invention include, but are not limited to, DDD, DDDR, VDD, VDDR, DDI, DDIR, DVI, DVIR, VVI and VVIR.

Figure 4C:
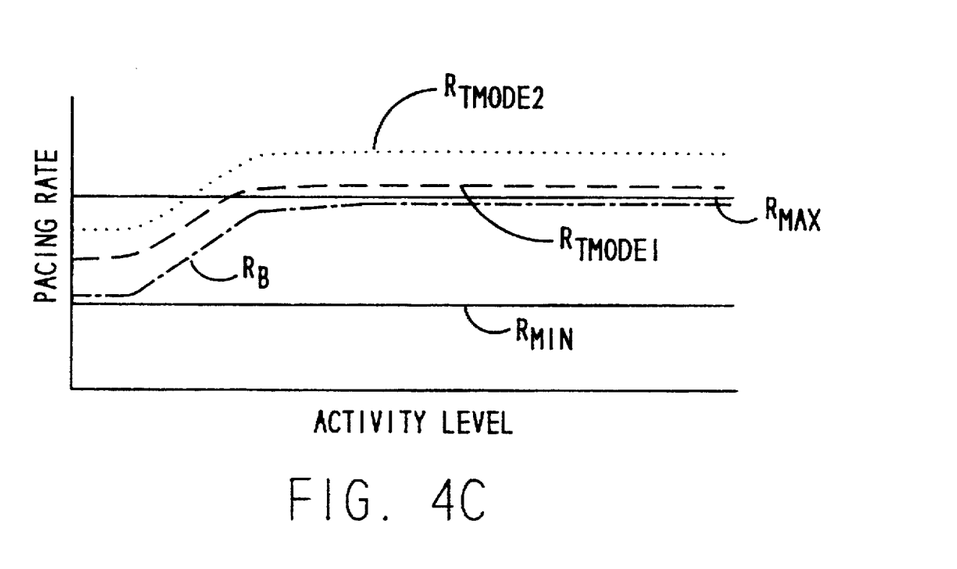
FIG. 4C is a plot showing a second alternative embodiment of the relationship between the mode switching rate and the base pacing rate.
Figure 6:
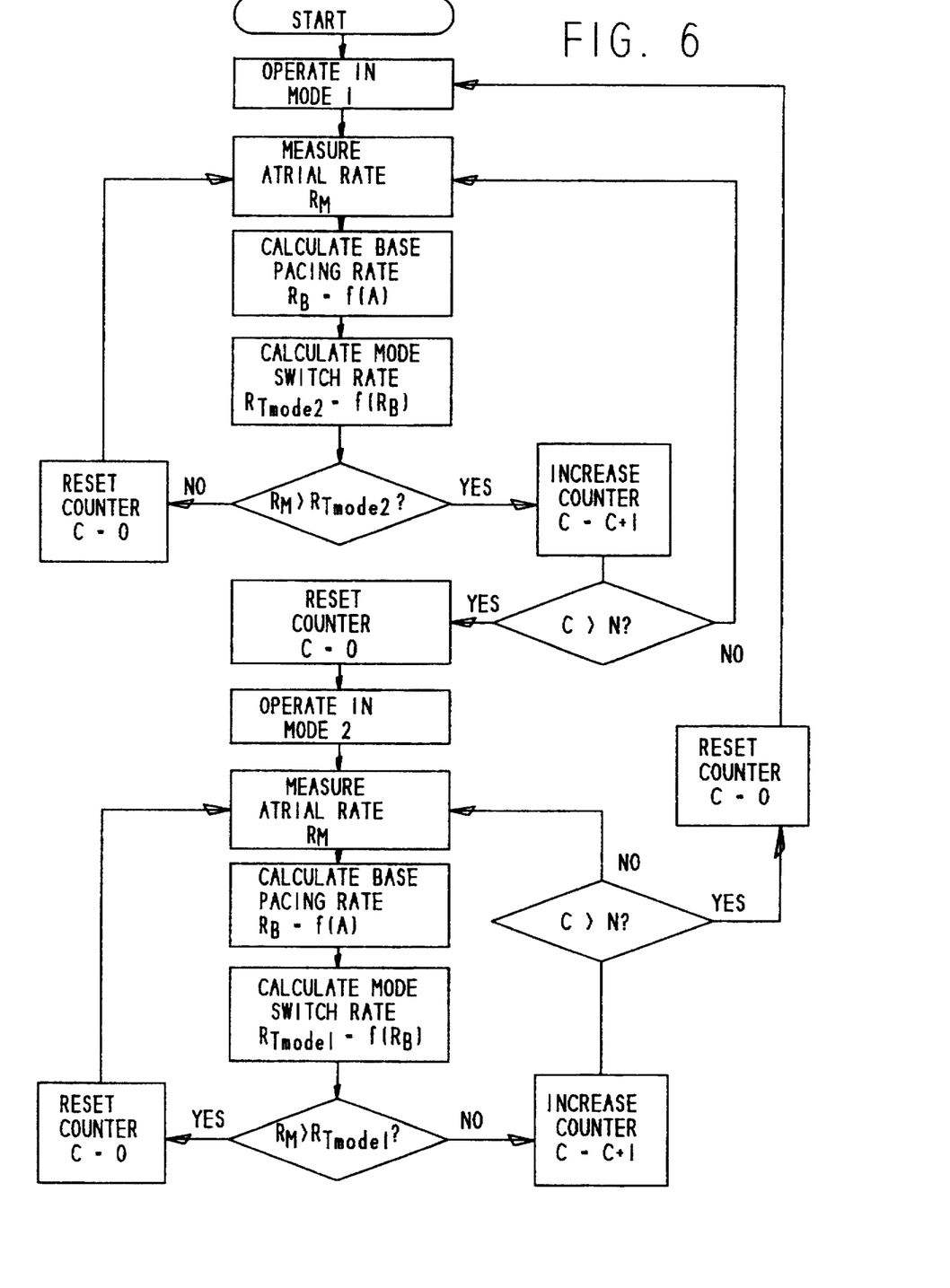
FIG. 6 is a flow chart representing the program steps associated with operating a pacer in accordance with another embodiment of the present invention.

In another preferred embodiment, a moderating effect is used in conjunction with the aforementioned mode switching threshold rate, so that while switching from the first pacing mode to the second occurs at one threshold, the switch back from the second pacing mode to the first occurs at a different, lower threshold. The logic routine for this embodiment is shown in FIGS. 6 and a plot showing the relationship between the base pacing rate and the two mode switch thresholds is shown in FIG. 4C. In this embodiment, the two mode switch thresholds, $R_{Tmode2}$ and $R_{Tmode1}$, are calculated as functions of $R_B$ using preprogrammed algorithms that are analogous to the algorithm used in the embodiment of FIG. 5 to calculate $R_T$. The first, $R_{Tmode2}$, is used in the manner described above with respect to FIG. 4A to determine whether the measured atrial rate $R_M$ has risen to a level at which operation in Mode 2 is appropriate. Once the pacer has switched to Mode 2, a second threshold rate $R_{Tmode1}$, which is lower than $R_{Tmode2}$, is calculated. The measured atrial rate $R_M$ is then compared to $R_{Tmode1}$, and the switch back to Mode 1 does not occur unless $R_M$ is less than $R_{Tmode1}$. Counters are used as shown and described above, to ensure that switching does not occur unless the threshold has been crossed by n consecutive beats. In this way, a restraint on switching is achieved and the pacer is less likely to toggle rapidly between the two modes.

The present invention provides a technique for varying the automatic mode switch rate so that the operation of the pacemaker can more precisely meet the pacing needs of the body in which it is implanted. While preferred embodiments of this invention have been shown and described, modifications thereof can be made by one skilled in the art without the departing from the spirit or teaching of this invention. Accordingly, the scope of the protection is not limited to the embodiments described herein, but is only limited by the claims which follow, the scope of which shall include all equivalents of the subject matter of the claims.

What is claimed is:

1. A method of operating a programmable rate-responsive pacemaker in a heart, comprising the steps of:

(a) programming the pacemaker with a mode switching threshold rate calculating algorithm;

(b) measuring a value of at least one physiologic indicator and using the measured value to calculate an activity level A;

(c) calculating a first mode switching threshold rate $R_T$ based on the activity level A;

(c) measuring the atrial rate $R_M$;

(d) comparing the measured atrial rate $R_M$ to the first mode switching threshold rate $R_T$;

(e) operating in a first mode of operation when the measured atrial rate $R_M$ is less than the mode switching threshold rate $R_T$; and (f) operating in a second mode of operation when the measured atrial rate $R_M$ is greater than the mode switching threshold rate $R_T$.

2. The method according to claim 1, further including the step of calculating a base pacing rate $R_B$ that is a function of activity level A.

3. The method according to claim 2 wherein $R_T$ is a function of $R_B$.

4. The method according to claim 2 wherein $R_T = R_B + c$, where c is a constant.

5. The method according to claim 2 wherein $R_T = R_B + c$, where c is a function of A.

6. The method according to claim 2 wherein $R_T = R_B + c_1 (A_2 - A) + c_2$ for $A_1 < A < A_2$, where $A_1$ and $A_2$ are predetermined constants.

7. The method according to claim 6 wherein $R_T = R_B + (c_1 + c_2)$ for $A < A_1$ and $R_T = R_B + c_2$ for $A > A_2$.

8. The method according to claim 1 wherein the mode of operation selected in step (e) is selected from the group of modes consisting of DDD, DDDR, VDD, VDDR, DDI, DDIR, DVI, and DVIR.

9. The method according to claim 1 wherein the mode of operation selected in step (f) is VVI.

10. The method according to claim 1 wherein the mode of operation selected in step (f) is VVIR.

11. The method according to claim 1 wherein the mode of operation selected in step (f) is DDI.

12. The method according to claim 1 wherein the mode of operation selected in step (f) is DDIR.

13. The method according to claim 1 wherein the physiologic indicator is selected from the group consisting of: motion, body temperature, blood oxygen, respiratory rate, minute volume and Q-T interval.

14. The method according to claim 1 wherein the selection of the first mode occurs only when the measured atrial rate $R_M$ is less than the mode switching threshold rate $R_T$ for more than a predetermined number of beats n.

15. The method according to claim 1 wherein the selection of the first mode occurs only when the measured atrial rate $R_M$ Is greater than the mode switching threshold rate $R_T$ for more than a predetermined number of beats n.

16. A method of operating a programmable rate-responsive pacemaker that is capable of operating in at least two modes of operation in a heart, comprising the steps of:
    (a) programming the pacemaker with a mode switching threshold rate calculating algorithm;
    (b) measuring at least one physiologic indicator and using the measured value to calculate an activity level A;
    (c) measuring the atrial rate $R_M$;
    (d) calculating a first mode switching threshold rate $R_{Tmode2}$ based on the activity level A;
    (e) comparing the measured atrial rate $R_M$ to the first mode switching threshold rate $R_{Tmode2}$;
    (f) calculating a second mode switching threshold rate $R_{Tmode1}$ based on the activity level A;
    (g) comparing the measured atrial rate $R_M$ to the second mode switching threshold rate $R_{Tmode1}$;
    (h) switching to a second operating mode if the pacer is in a first mode of operation and the measured atrial rate $R_M$ is greater than the mode switching threshold rate $R_{Tmode2}$; and
    (i) switching to a first operating mode if the pacer is in a second mode of operation and the measured atrial rate $R_M$ is less than the mode switching threshold rate $R_{Tmode1}$.

17. The method according to claim 16 wherein the first operating mode is selected from the group of modes consisting of DDD, DDDR, VDD, VDDR, DDI, DDIR, DVI, and DVIR.

18. The method according to claim 17 wherein $R_{Tmode1}$ is a function of a base pacing rate $R_B$.

19. The method according to claim 16 wherein the second operating mode is VVI.

20. The method according to claim 16 wherein the second operating mode is VVIR.

21. The method according to claim 16 wherein the second operating mode is DDI.

22. The method according to claim 16 wherein the second operating mode is DDIR.

23. The method according to claim 16 wherein the physiologic indicator is selected from the group consisting of: motion, body temperature, blood oxygen, respiratory rate, minute volume and Q-T transfer.

24. The method according to claim 16 wherein $R_{Tmode2}$ is a function of a base pacing rate $R_B$.

25. A pacer comprising:
    a sensor for sensing physiologic indicators and sending an indicator signal;
    a memory device for storing at least one predetermined switching algorithm and at least two pacing modes;
    an atrial rate monitor for generating an atrial rate signal; and
    a microprocessor for receiving said indicator signal and said atrial rate signal and calculating a measured atrial rate $R_M$ based on said atrial rate signal, an activity level A based on said indicator signal, a base pacing rate $R_B$ that is a function of A and a mode switching threshold rate $R_T$ that is a function of A , said microprocessor causing said pacer to switch between pacing modes as a result of a comparison of said measured atrial rate $R_M$ and said mode switching threshold rate $R_T$.

* * * * *